United States Patent [19]

Schalk et al.

[11] Patent Number: 5,637,803
[45] Date of Patent: Jun. 10, 1997

[54] DEVICE FOR MONITORING THE PRESSURE IN SEVERAL ANALYSIS VESSELS

[75] Inventors: Andreas Schalk; Peter Kettisch, both of Graz; Johannes Zach, St. Marein; Helmut Sinabell, Graz, all of Austria

[73] Assignee: Anton Paar KG, Graz-Strassgang, Austria

[21] Appl. No.: 420,725

[22] Filed: Apr. 10, 1995

[30] Foreign Application Priority Data

Apr. 18, 1994 [DE] Germany ............... 44 13 425.8

[51] Int. Cl.[6] ........................................... G01L 7/16
[52] U.S. Cl. ..................... 73/744; 73/703; 73/716; 73/705; 60/567
[58] Field of Search ................ 73/706, 744, 745, 73/715, 716, 717, 723, 705; 60/567; 91/33, 52

[56] References Cited

U.S. PATENT DOCUMENTS

| | | |
|---|---|---|
| 2,943,605 | 7/1960 | Broders . |
| 3,100,997 | 8/1963 | Lorenz . |
| 4,248,831 | 2/1981 | Hughes . |
| 4,401,625 | 8/1983 | Willay et al. . |
| 4,726,190 | 2/1988 | Van Marcke ...................... 60/567 |
| 5,127,269 | 7/1992 | Grudzien ...................... 73/723 X |
| 5,230,865 | 7/1993 | Hargett et al. . |
| 5,264,185 | 11/1993 | Floyd . |

FOREIGN PATENT DOCUMENTS

| | | |
|---|---|---|
| 26 18969 | 11/1977 | Germany . |
| 31 41939 | 5/1983 | Germany . |
| 299400 | 10/1983 | Germany . |
| 36 00090 | 7/1987 | Germany . |
| 36 20381 | 1/1988 | Germany . |
| 38 18697 | 12/1989 | Germany . |
| 39 19601 | 12/1989 | Germany . |
| 41 14525 | 8/1992 | Germany . |
| 41 08766 | 9/1992 | Germany . |
| 43 00957 | 7/1994 | Germany . |
| 94 06553 | 3/1994 | WIPO . |

OTHER PUBLICATIONS

Kojima et al., "Microwave digestion of biological samples with acid mixture in a closed double PTFE vessel for metal determination by one-drop flame atomic absorption spectrometry," *Analytica Chimica Acta*, 264:101–106, 1992.

Kojima et al, "Vapour-phase acid decomposition of high pure silicas in a sealed PTFE bomb and determination of impurities by one-drop atomic spectrometry," *Analytica Chimica Acta*, 245:35–41, 1991.

Buback, "Spektroskopie an fluiden Phasen–das Studium chemischer Reaktionen und Gleichgewichte bis zu hohem Druck," *Angew. Chem.*, 103:658–670, 1991.

Matusiewicz, "Development of a High Pressure/Temperature Focused Microwave Heated Teflon Bomb for Sample Preparation," *Anal. Chem.*, 66:751–755, 1994.

Lopez-Avila et al., "Microwave–Assisted Extraction of Organic Compounds from Standard Reference Soils and Sediments," *Anal. Chem.*, 66:1097–1106, 1994.

*Primary Examiner*—George M. Dombroske
*Assistant Examiner*—Joseph L. Felber
*Attorney, Agent, or Firm*—Rothwell, Figg, Ernst & Kurz, P.C.

[57] ABSTRACT

The present invention concerns a device for monitoring the pressure in at least two pressure-tight analysis vessels, that have been sealed by means of lids, whereby heat is supplied to the analysis vessels by means of a heating apparatus. The internal pressure of the analysis vessel acts on its lid. The lid is connected to a piston in a closed hydraulic system. The force, that is dependent on the internal pressure of the analysis vessel, is transferred by the lid to the piston in the hydraulic system. A lid and a piston are assigned to every analysis vessel. In addition, a stop device is assigned to each piston, whereby the stop device limits the outward movement of the piston in the event of excess pressure in the hydraulic system relative to the internal pressure of the analysis vessel. The pistons are connected to one another via the hydraulic system.

16 Claims, 3 Drawing Sheets

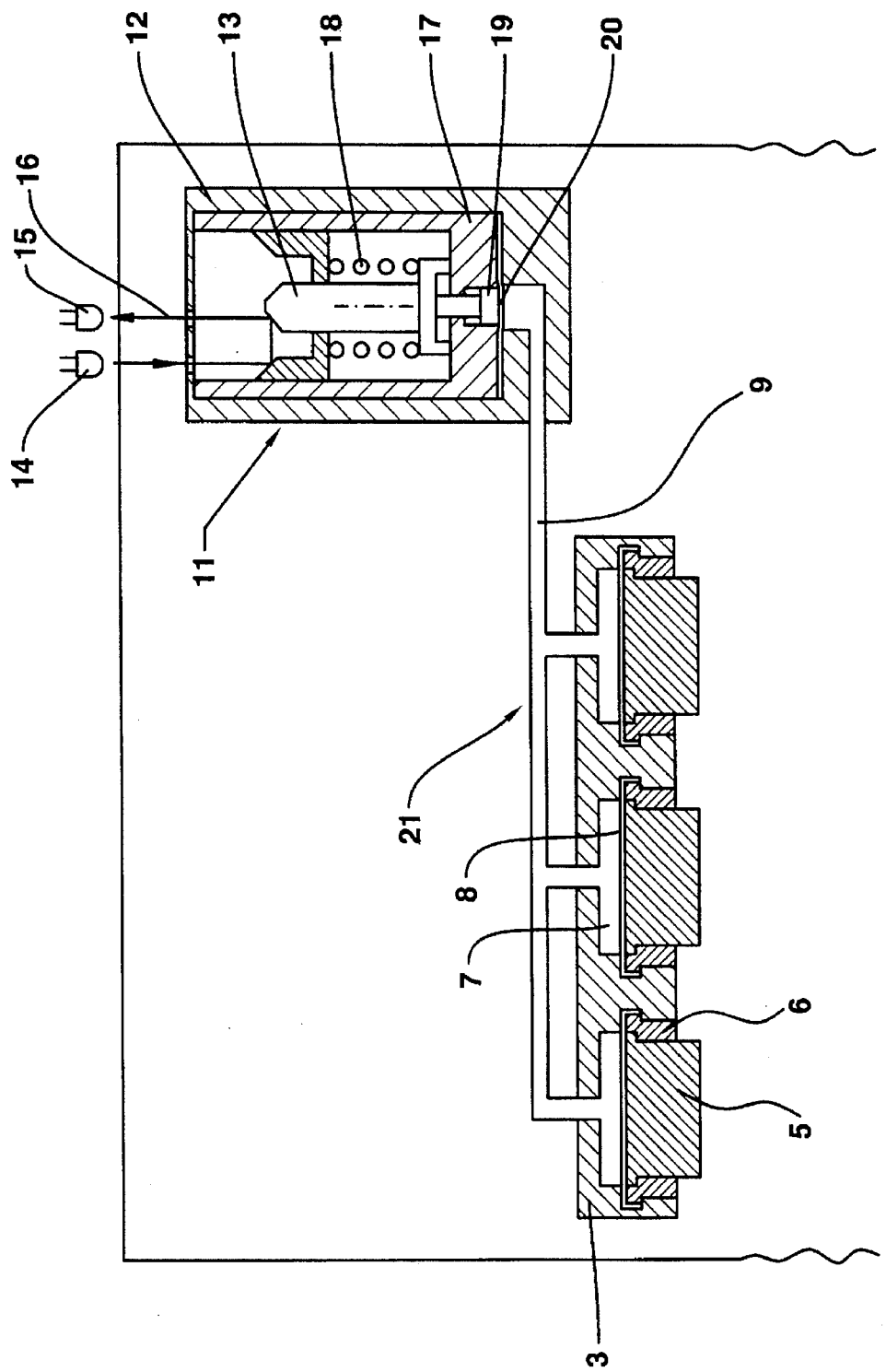

DEVICE FOR MONITORING THE PRESSURE IN SEVERAL ANALYSIS VESSELS

FIELD OF THE INVENTION

The present invention concerns a device for monitoring the pressure in at least two pressure-tight analysis vessels, that are sealed by means of lids, whereby heat is supplied to the analysis vessels by means of a heating apparatus and whereby the internal pressure of the analysis vessel acts on the lid.

BACKGROUND OF THE INVENTION

A main task of chemical analysis comprises the determination of the composition of an unknown sample material. Thus, by way of example, the molecular formula of a chemical compound is determined in an elemental analysis. In various analysis procedures, especially elemental analysis, it is necessary, in an initial working step, to decompose the substance, that is to be investigated, either completely or partially, into the smallest element-specific molecules or ions. In the case of so-called acidic analysis, this degradation process is carried out with the help of one or more acids, oxidizing agents or other aggressive chemical substances. The fragments that are produced can be determined quantitatively and qualitatively in analysis steps that follow on therefrom. In acidic analysis, it is known that the yield can be significantly improved and the reaction time for the degradation of the substance can be drastically reduced by using high pressures and high temperatures. Thus, in addition to open analysis, analysis is frequently carried out under conditions of increased pressure and temperature. In order to reach the reaction temperatures, use is made of heating apparatus that, for example, utilize thermal radiation, thermal conduction or microwave energy.

The closed analysis vessels cannot withstand any arbitrarily high pressure and, as a rule, they are therefore equipped with a safety valve. The safety valve opens if the internal pressure exceeds a prescribed limiting value in the analysis vessel. During the opening of the safety valve, a portion of the substances, that are contained in the analysis vessel, escapes. An analysis vessel is described in DE 39 19 601 whose internal pressure acts on a pressure recorder that is connected to a control unit for the heating apparatus. As a result, one ensures that the heating apparatus is switched off before the upper pressure limit is reached.

If use is made of several analysis vessels with a communal heating apparatus, then the problem presents itself of monitoring the upper pressure limit for each individual vessel since different pressures arise in the individual analysis vessels especially as a result of exothermic reactions.

In German patent specification DE-OS 38 18 697, an attempt is made to solve the problem by using an individual reference vessel for the measurement of pressure. In the case of different pressures in the analysis vessels, the situation can arise that some of the analysis vessels release their pressure via a safety valve before the upper pressure limit has been reached in the reference vessel and this leads to the switching off of the heating apparatus. This leads to losses of the sample. In the same way, the situation can also arise whereby the upper pressure limit is reached in the reference vessel and the heating apparatus is switched off before the required reaction temperature has been reached in the other vessels.

One possibility for solving the problem of monitoring the pressure in several analysis vessels comprises the feature that each individual vessel is equipped with a pressure measurement device that is connected to the control unit for the heating apparatus. However, this solution is associated with considerable costs.

If microwave energy is used for heating, then a further problem resides in the feature that the electrical lines that are used in, for example, transferring the measurements from the pressure recorder to the control unit for the heating apparatus are capable of absorbing microwave energy or causing interference in a microwave field. This has particularly disadvantageous effects if several analysis vessels are used simultaneously. The microwave field that is used for heating several analysis vessels is then no longer uniform and different amounts of heat are supplied to the individual analysis vessels. Although it is possible to shield the electrical lines with respect to the microwave field, this procedure is nevertheless time-consuming and costly. In addition, resonance positions in the microwave field can generate flash-over phenomena at the connections of the electrical lines.

SUMMARY OF INVENTION

The task of the present invention is to provide a device by which the pressure can be monitored simultaneously in several heated, pressure-tight analysis vessels without one's needing a dedicated pressure measurement device for each analysis vessel. In addition, no interference in a microwave field, that is possibly used for heating the samples, should be produced as a result of the supply of energy to the pressure measurement device and the transfer of the measurements to a control unit.

This task is accomplished by a device for monitoring the pressure in at least two pressure-tight analysis vessels that are sealed by means of lids, whereby heat is supplied to the analysis vessels by means of a heating apparatus. The internal pressure of the analysis vessel acts on its lid. The lid is connected to a piston in a closed hydraulic system. The force, that is dependent on the internal pressure of the analysis vessel, is transferred from the lid to the piston of the hydraulic system. A lid and a piston are assigned to each analysis vessel. In addition, a stop device is assigned to each piston, whereby the stop device limits the outward movement of the piston in the event of excess pressure in the hydraulic system relative to the internal pressure of the analysis vessel. The pistons are connected to one another via the hydraulic system. If the internal pressure increases in an analysis vessel A, then the associated piston A is impacted by a force and moves outward. The other pistons are pressed against their stop device. A pressure then prevails in the hydraulic system that corresponds to the internal pressure in the analysis vessel A. As soon as the internal pressure in one of the other analysis vessels, e.g. analysis vessel B, exceeds the internal pressure in analysis vessel A, piston B moves outward and piston A is pressed against its stop device. The pressure in the hydraulic system then corresponds to the internal pressure in analysis vessel B. By means of the device in accordance with the invention, one ensures that the pressure in the hydraulic system always corresponds to the highest internal pressure in the analysis vessels that are used. Consequently, the upper pressure limit of all the analysis vessels that are used can be monitored by means of one single pressure measurement device that is connected to the hydraulic system. In the simplest case, the pressure measurement device is connected to the switching device of the heating apparatus in such a way that the output of heat is reduced as soon as the upper pressure limit has been reached in one of the analysis vessels.

The analysis vessel, that has been tightly sealed with a lid, is advantageously arranged in a pressure resistant and temperature resistant outer container with a cap that is detachably connected thereto. In this way, the piston of the hydraulic system is guided into the cap of the external container. A hydraulic cylinder for the piston is provided above the lid. The hydraulic cylinder communicates with the other analysis vessels and with the pressure measurement device via a hydraulic line.

The piston is advantageously separated from the hydraulic liquid by means of an elastic membrane that is arranged in the hydraulic cylinder. The elastic membrane prevents the hydraulic liquid from escaping. In this way, the elasticity of the membrane ensures that the piston transfers the internal pressure of the analysis vessel to the hydraulic system.

The hydraulic system advantageously has several arms that extend radially outward toward the analysis vessels from a center in which the pressure measurement device has been arranged. In this way, the analysis vessels that have been arranged in the outer containers, the hydraulic system and the pressure measurement device form a complex unit that is held together between two flanges by means of nut/bolt connections. One nut/bolt connection is advantageously provided per analysis vessel. Means for the attachment of the flange to a rotatable counter can be arranged in the center of the lower flange. On heating, it is possible, as a result of this, to set in rotary motion the unit that has been formed from the analysis vessels, the hydraulic system and the pressure measurement device. Irregularities in an energy field, that is used for heating, can be compensated as a result of the continuous rotation of the centro-symmetrically arranged analysis vessels.

The heating apparatus is preferably a microwave oven. The analysis vessels and the pressure measurement device are arranged in the microwave field that is produced by the microwave oven. The pressure measurement device is advantageously surrounded by a closed microwave-tight housing. The housing has been constructed in such a way that it forms an impermeable screen for the microwave field. A microwave-free zone is formed in the interior of the housing. The housing causes only slight interference in regard to the distribution of microwaves. It is meaningful to arrange the housing in such a way in the microwave field that the slight interference that is produced is distributed in equal portions over all the analysis vessels. In this way, one ensures that all the analysis vessels are supplied with the same amount of energy.

An energy source for the pressure measurement device is advantageously arranged in the closed microwave-tight housing. A battery, an accumulator or a condenser with a high capacity can serve as a source of energy. This arrangement has the advantage that no electrical lines are required for the supply of energy to the pressure measurement device.

The pressure measurement device is advantageously connected to a source of energy outside of the closed microwave-tight housing via a non-electrical line. Interference with the microwave field is avoided as a result of the use of non-electrical lines for the supply of energy. One can, for example, arrange solar cells in the microwave-tight housing whereby the solar cells are supplied with light energy from outside of the housing.

An energy converter, which can be represented by reference numeral 23 in FIG. 2, is advantageously arranged in the closed microwave-tight housing for the conversion of microwave energy into electrical energy. In this way, a microwave-permeable zone is provided in the otherwise microwave-tight housing, whereby microwave energy can reach the energy converter through the microwave-permeable region. In this way, the microwave energy that is required for heating the analysis vessels can also be used to operate the pressure measurement device.

A generator, which alternatively can be represented by reference numeral 23 in FIG. 2, is advantageously arranged in the closed microwave-tight housing, whereby the generator is driven mechanically from outside of the housing.

The pressure measurement device is advantageously connected to a control unit 24 for the microwave oven, whereby the control unit is arranged outside of the microwave field that is produced by the microwave oven. The control unit serves in reducing the output of heat as soon as the upper pressure limit has been reached in one of the analysis vessels.

A light transmitter is advantageously arranged in the pressure measurement device, whereby the light transmitter serves in the opto-electrical transfer of the measurements to a receiver that is arranged outside of the pressure measurement device and whereby the receiver is connected to the control unit for the heating apparatus. In this way, the measurements can be transferred to the control unit in a non-electrical manner without causing interference in the microwave field.

The transmitter and the receiver are advantageously connected via a light conductor.

The pressure measurement device is advantageously connected to the control unit via a heat conductor or via a hydraulic line 25.

The pressure measurement device preferably communicates with the hydraulic system via a plunger, whereby the head of the plunger is separated from the hydraulic system by means of an elastic membrane.

The plunger is advantageously impacted by a spring-like force against the pressure of the hydraulic system. The housing has a stop device that limits the movement of the plunger in the direction of the membrane. The end of the plunger, that is opposite the head, has a mirror-polished tip. In addition, a light transmitter and a light receiver are arranged in such a way in the pressure measurement device that a beam of light that leaves the light transmitter is led to the light receiver via the mirror-polished tip of the plunger. The highest internal pressure of the various analysis vessels is measured, in each case, by means of this pressure measurement device. The higher the pressure in the hydraulic system—whereby this pressure corresponds to the highest internal pressure of all the analysis vessels that are connected thereto—the farther the plunger is pressed into the housing. The light beam is reflected differently at the mirror-polished plunger tip in a way that depends on the depth of penetration of the plunger. The plunger can also be arranged in such a way that, in its starting position, its mirror-polished tip is not yet struck by the beam of light but is struck only starting from a certain depth of penetration of the plunger. This means that the pressure is measured only if a prescribed minimum value has been exceeded. The beam of light is reflected from the tip of the plunger toward the light receiver. The light receiver detects the pressure-dependent deflection of the beam of light. The information that is obtained in this way is transferred in a non-electrical manner to the control unit for the heating apparatus. As a result of the form of construction of the device in accordance with the invention, one ensures that, on each occasion, the highest internal pressure of all the analysis vessels that are used is measured by means of only one pressure measurement device.

Interference with the microwave field is avoided as a result of the non-electrical supply of energy to the pressure measurement device and the non-electrical transfer of the measurements to the control unit.

The light transmitter and/or the light receiver are advantageously arranged outside of the microwave field that is produced by the microwave oven. In the case of this form of embodiment, one can dispense with the microwave-tight form of construction of the housing of the pressure measurement device.

BRIEF DESCRIPTION OF THE DRAWINGS

Using the attached drawing, various forms of embodiment of the device in accordance with the invention are elucidated in more detail, by way of example, in the following sections.

The following aspects are shown in this connection:

FIG. 4 shows a side view in sectional form through the pressure measurement device.

DETAILED DESCRIPTION OF THE PREFERRED EMBODIMENTS

Figure 1:
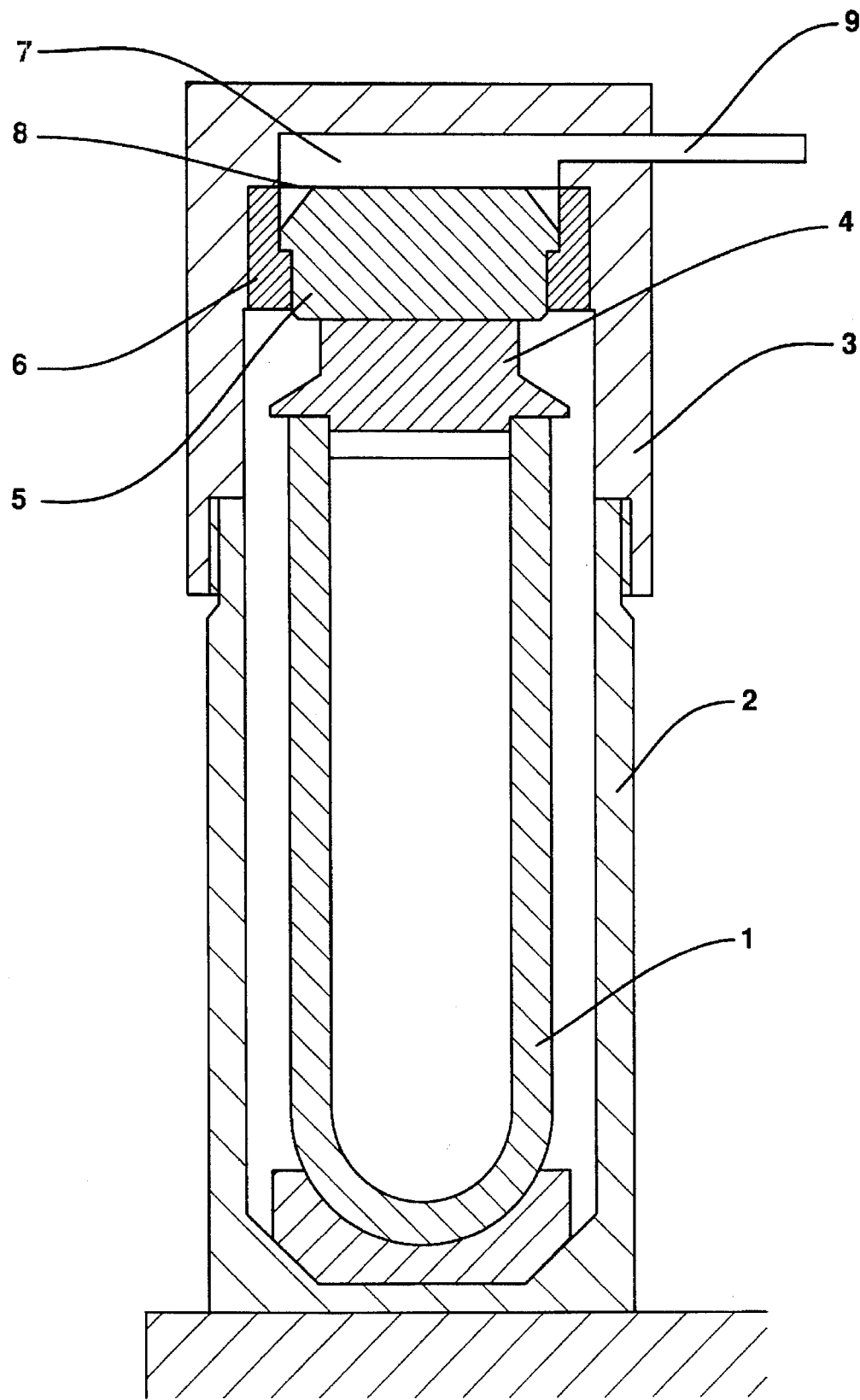
FIG. 1 shows an analysis vessel, whereby the piston of the device in accordance with the invention has been arranged in the cap of an outer container that surrounds the analysis vessel.

FIG. 1 shows an analysis vessel, 1 that is surrounded by an outer container 2, with a cap 3. The internal pressure of the analysis vessel 1 acts on a lid 4 that presses against the piston 5 in the event of increasing internal pressure in the analysis vessel 1 with maintenance of its sealing action. A hydraulic cylinder 7 for the piston 5 is located above the lid 4, whereby the hydraulic cylinder 7 has been filled with a hydraulic liquid. The hydraulic cylinder 7 is separated from the piston 5 by means of an elastic membrane 8. The hydraulic cylinder 7 is connected to a pressure measurement device via a hydraulic line 9.

An increase in the internal pressure in the analysis vessel 1 is therefore transferred to the hydraulic liquid in the hydraulic cylinder 7. In the case of the form of embodiment that is shown in FIG. 1, the piston 5 is arranged in the cap 3 of the outer container 2.

Figure 2:
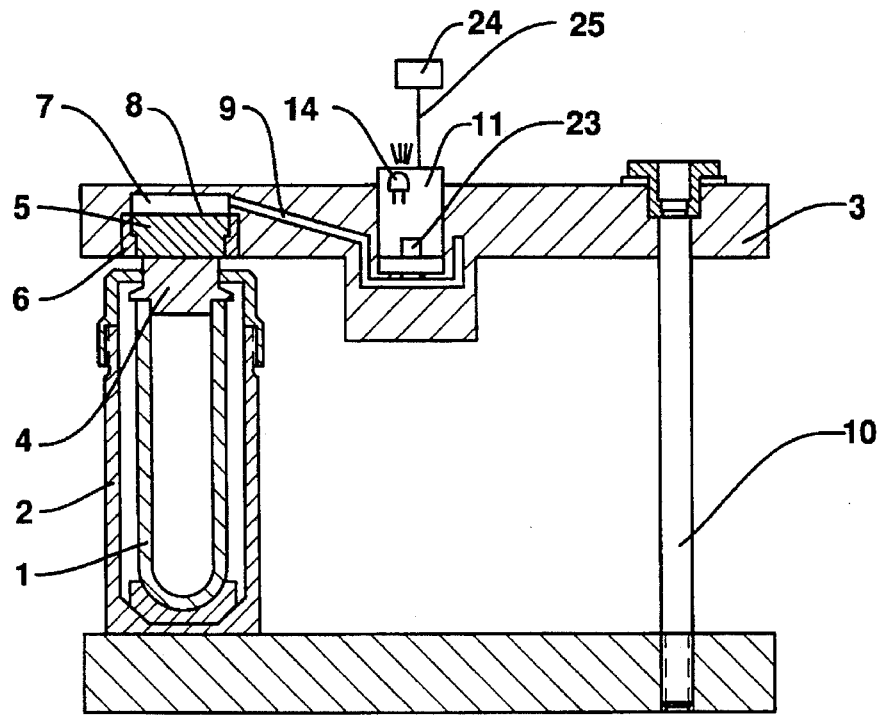
FIG. 2 shows a section through a form of embodiment of the device in accordance with the invention along the line A–B in FIG. 3.
Figure 3:
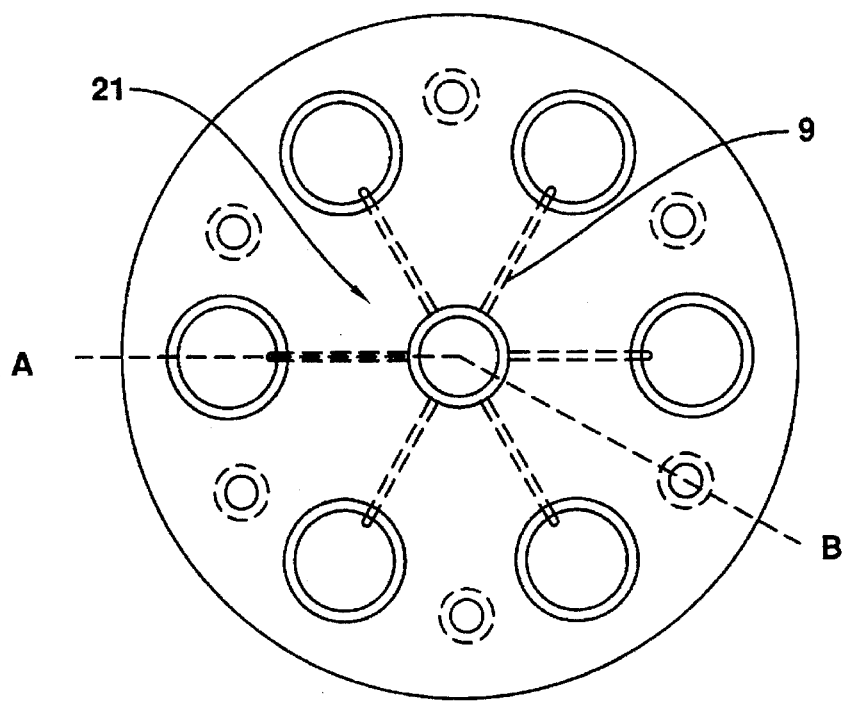
FIG. 3 shows a plan view in sectional form through the device that is shown in FIG. 2

However, the piston 5 can also be arranged for pressure monitoring in the device that is shown in FIG. 2. The hydraulic cylinder 7 is connected to the pressure measurement device 11 via a hydraulic line 9. In this way, a change in the internal pressure in the analysis vessel 1 is transferred to the pressure measurement device 11 via the lid 4, the piston 5 and the hydraulic liquid. The device that is shown in FIG. 3 has been designed to monitor the pressure in six analysis vessels. Every analysis vessel 1 has a piston 5 assigned to it. The pistons 5 are connected to one another via the hydraulic system (21). The hydraulic system (21) is impacted by the desired pressure prior to setting the device in action, preferably a pressure that corresponds to the possible critical pressure of the analysis vessels under the conditions of the analysis. In this condition, the pressure in the hydraulic system (21) is higher than the internal pressure in the analysis vessels 1. In this way, the pistons 5 are pressed, in each case, against a stop device 6. As soon as the internal pressure in one of the analysis vessels 1 exceeds the value that was originally set up, the piston 5 that is connected to this analysis vessel becomes separated from the associated stop device 6. As a result of the arrangement of the stop devices 6 and the pistons 5 in the hydraulic system (21) in accordance with the invention, one ensures that a pressure always prevails in the hydraulic system (21) that corresponds to the highest internal pressure of all the connected analysis vessels 1. On exceeding the critical pressure, the output of heat is reduced. The device for pressure monitoring in FIG. 2 and 3 is held together by a bolt/nut connection 10.

In the form of embodiment shown in FIGS. 2 and 3, the analysis vessels 1 that are arranged in the outer containers 2, the hydraulic system (21) and the pressure measurement device 11 form a complex unit. The centro-symmetrically arranged analysis vessels 1 are fixed between two flanges by means of bolt/nut connections 10. In this way, the hydraulic system (21) has several arms 9 that extend radially outward toward the analysis vessels from a center in which the pressure measurement device 11 has been arranged. One bolt/nut connection is advantageously provided per analysis vessel 1. In the center of the lower flange, means (not shown) are arranged for attaching the flange to a counter that is capable of rotation.

The pressure measurement device 11, that is shown in FIG. 4, has a microwave-tight housing 12. The dashed/dotted line indicates the extension of the microwave field in the region of the head of the device. The pressure measurement device communicates with the hydraulic system 21 via a plunger 13, whereby the head 19 of the plunger 13 is separated from the hydraulic system 21 by means of an elastic membrane 20. This ensures that no hydraulic liquid from the hydraulic system (21) gets into the pressure measurement device 11. The plunger 13 is impacted by a spring-like force against the pressure of the hydraulic system. A stop device is provided that limits the movement of the plunger 13 in the direction of the membrane 20. The pre-tension force of the spring 18 is selected in such a way that the plunger 13 lifts up from the stop device 17 as soon as the pressure in the hydraulic system (21) exceeds the initial tensile force of the spring 18.

The tip of the plunger 13 has been mirror polished. A light transmitter 14 and a light receiver 15 are arranged outside of the housing 12. A beam of light 16, that is sent out by the light transmitter 14, is reflected toward the light receiver 15 by the mirror polished tip of the plunger 13. The beam of light 16 is deflected differently at the mirror polished tip of the plunger 13 in a way that depends on how far the plunger 13 has lifted up from the stop device 17. The deflection of the beam of light 16 and/or the change in its recorded intensity are a measure of the pressure in the hydraulic system (21) and are also, consequently, a measure of the highest internal pressure in the connected analysis vessels 1. The light receiver 15 can consist of one or more receiver diodes. The light receiver and the light transmitter 14 can also be arranged inside the microwave-tight housing 12 (see FIGS. 2 and 4).

We claim:

1. Device for monitoring the pressure in at least two pressure-tight analysis vessels, that have been sealed by means of lids, whereby heat is supplied to the analysis vessels via a heating apparatus, characterized by the feature that each lid (4) of the analysis vessels (1) is connected to a piston (5) in a closed hydraulic system (21), whereby each piston (5) has a stop device (6) assigned to it that limits resultant movement of the piston (5) in the event of excess pressure in the hydraulic system (21) relative to the internal pressure of the analysis vessels (1) and whereby the pistons (5) communicate with one another via the hydraulic system (21) and a pressure measurement device (11) is connected to the hydraulic system (21).

2. Device in accordance with claim 1, whereby the analysis vessels, that have been tightly sealed with lids, are arranged in a pressure resistant outer container with a cap that is detachably connected thereto, characterized by the feature that the piston (5) of the hydraulic system (21) is arranged in the cap (3) of the outer container (2), that a hydraulic cylinder (7) for the piston (5) is provided above the lid (4) in the cap (3) and that the hydraulic cylinder (7) communicates with the pressure measurement device (11) via a hydraulic line (9).

3. Device in accordance with claim 2, characterized by the feature that a hydraulic liquid in the cylinder (7) is separated from the piston (5) by means of an elastic membrane (8).

4. Device in accordance with claim 1, characterized by the feature that the hydraulic system (21) has several arms (9) that extend radially outward toward the analysis vessels (1) from a center in which the pressure measurement device (11) has been arranged.

5. Device in accordance with claim 1, characterized by the feature that the heating apparatus is a microwave oven and the pressure measurement device (11) is arranged in a closed microwave-tight housing (12).

6. Device in accordance with claim 5, characterized by the feature that a source of energy for the pressure measurement device (11) is arranged in the closed microwave-tight housing (12).

7. Device in accordance with claim 6, characterized by the feature that the pressure measurement device (11) is connected to a control unit for the microwave oven, whereby the control unit is arranged outside of the microwave field that is produced by the microwave oven.

8. Device in accordance with claim 7, characterized by the feature that a transmitter for light has been arranged in the pressure measurement device (11), whereby the transmitter for light serves in transferring measurements to a receiver that is arranged outside of the pressure measurement device (11) and whereby the receiver is connected to the control unit for the heating apparatus.

9. Device in accordance with claim 8, characterized by the feature that the transmitter and receiver are connected via a light conductor.

10. Device in accordance with claim 7, characterized by the feature that the pressure measurement device (11) is connected to the control unit via a hydraulic line.

11. Device in accordance with claim 6; characterized by the feature that the pressure measurement device (11) communicates with the hydraulic system (21) via a plunger (13), whereby the head (19) of the plunger (13) is separated from the hydraulic system (21) by means of an elastic membrane (20).

12. Device in accordance with claim 11, characterized by the feature that the plunger (13) is impacted by means of a spring-like force against the pressure of the hydraulic system (21) and a stop device (17) is provided that limits the movement of the plunger (13) in the direction of the membrane (20) and whereby the end of the plunger (13), that is opposite the head (19), has a mirror polished tip and that a light transmitter (14) and a light receiver (15) are arranged in such a way in the pressure measurement device (11) that a beam of light (16), that is sent out by the light transmitter (14), is led, via the mirror polished tip of the plunger (13), to the light receiver (15).

13. Device in accordance with claim 5, characterized by the feature that the pressure measurement device (11) is connected via a non-electrical line to a source of energy outside of the closed microwave-tight housing (12).

14. Device in accordance with claim 13, characterized by the feature that a light transmitter (14) and/or a light receiver (15) are arranged outside of the microwave field that is produced by the microwave oven.

15. Device in accordance with claim 5, characterized by the feature that an energy converter for the conversion of microwave energy into electrical energy has been arranged in the closed microwave-tight housing (12), whereby a microwave-permeable zone has been provided in the housing (12).

16. Device in accordance with claim 5, characterized by the feature that a generator has been arranged in the closed microwave-tight housing (12).

* * * * *